US011672683B2

(12) United States Patent
Khan (10) Patent No.: US 11,672,683 B2
(45) Date of Patent: Jun. 13, 2023

(54) BIFUNCTIONAL BALLOON-EXPANDABLE AND SELF-EXPANDABLE STENT (71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Muhammad Fayaz Khan, Riyadh (SA)

(73) Assignees: National Guard Health Affairs, Riyadh (SA); King Saud bin Abdulaziz University, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 17/062,836

(22) Filed: Oct. 5, 2020

(65) Prior Publication Data
US 2022/0104955 A1  Apr. 7, 2022

(51) Int. Cl.
*A61F 2/954* (2013.01)
*A61F 2/958* (2013.01)
(Continued)

(52) U.S. Cl.
CPC ............. *A61F 2/954* (2013.01); *A61F 2/958* (2013.01); *A61F 2/962* (2013.01); *A61F 2/97* (2013.01); *A61L 31/022* (2013.01); *A61F 2002/821* (2013.01); *A61F 2002/9583* (2013.01); *A61F 2210/0004* (2013.01); *A61F 2210/0014* (2013.01); *A61F 2230/0069* (2013.01); *A61F 2250/001* (2013.01); *A61F 2250/0039* (2013.01); *A61F 2250/0048* (2013.01);
(Continued)

(58) Field of Classification Search
CPC ...... A61F 2250/0048; A61F 2250/0039; A61F 2/954
See application file for complete search history.

(56) References Cited

U.S. PATENT DOCUMENTS 6,168,621 B1 * 1/2001 Vrba .................. A61F 2/91
623/1.15
6,740,113 B2    5/2004 Vrba
(Continued)

OTHER PUBLICATIONS

Maciej Lesiak, "The Need For Dedicated Bifurcation Stents: A Critical Analysis", Interventional Cardiology Review, vol. 11, No. 2, Oct. 2016, pp. 124-127.
(Continued)

*Primary Examiner* — Rebecca S Preston
(74) *Attorney, Agent, or Firm* — Oblon, McClelland, Maier & Neustadt, L.L.P.

(57) ABSTRACT

A bifunctional expandable stent delivery assembly having a bifunctional expandable stent, a breakable cover, and a balloon. The bifunctional expandable stent has a balloon-expandable body portion and a self-expandable trumpet portion. The breakable cover fits over only the self-expandable trumpet portion and prevents self-expansion. The balloon is used to expand the balloon-expandable portion, which breaks the breakable cover and allows the self-expandable trumpet portion to self-expand. A method of stenting a patient using the bifunctional expandable stent delivery assembly is also provided.

20 Claims, 8 Drawing Sheets

(51) Int. Cl.
*A61F 2/97* (2013.01)
*A61L 31/02* (2006.01)
*A61F 2/962* (2013.01)
*A61F 2/82* (2013.01)

(52) U.S. Cl.
CPC ............... *A61F 2250/0067* (2013.01); *A61F 2250/0098* (2013.01)

(56) References Cited

U.S. PATENT DOCUMENTS

| | | |
|---|---|---|
| 6,945,994 B2 | 9/2005 | Austin et al. |
| 7,037,327 B2 | 5/2006 | Salmon et al. |
| 10,327,924 B2 | 6/2019 | Kelly |
| 2005/0228483 A1* | 10/2005 | Kaplan ............... A61F 2/915 623/1.15 |
| 2006/0265041 A1* | 11/2006 | Sanati ............... A61F 2/90 623/1.11 |
| 2007/0016280 A1* | 1/2007 | Yacoby ............... A61F 2/844 623/1.11 |
| 2009/0259293 A1* | 10/2009 | Moloney ............... A61F 2/86 623/1.16 |
| 2017/0014248 A1* | 1/2017 | Kelly ............... A61F 2/95 |
| 2018/0228626 A1 | 8/2018 | Kelly |

OTHER PUBLICATIONS

Konstantinos D. Rizas, et al., "Stent Polymers: Do they Make a Difference?", Circulation: Cardiovascular Interventions, vol. 9, No. 6, May 18, 2016, 32 pages.

Mamas A. Mamas, et al., "Use of the Sideguard (Cappella) stent in bifurcation lesions: a real-world experience", Eurointervention, vol. 7, No. 10, Feb. 2012, pp. 1170-1180 (Abstract only).

* cited by examiner

Closed cells
306

Open cells
307

Offset peak-to-peak
311

Mid-strut connectors
312

Peak-to-peak
313

Peak-to-valley
314

BIFUNCTIONAL BALLOON-EXPANDABLE AND SELF-EXPANDABLE STENT

BACKGROUND OF THE INVENTION

FIELD OF THE INVENTION

The present disclosure relates to a stent delivery assembly which includes as bifunctional expandable stent which has a balloon-expandable body portion and a self-expandable trumpet portion and a method for stenting a patient in need of percutaneous coronary intervention at a bifurcation site.

DISCUSSION OF THE BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cardiovascular disease is one of the largest health problems in the developed world. One of the more serious forms is Coronary Artery Disease (CAD), which typically occurs when part of the smooth, elastic lining inside a coronary artery becomes hardened, stiffened, and swollen with calcium deposits, fatty deposits, and abnormal inflammatory cells, leading to the formation of a plaque. This plaque can create an obstruction (known as a stenosis or a lesion) in an artery thereby blocking or restricting the normal supply of oxygenated blood to the heart muscle. This in turn can cause chest pain (angina), and ultimately can lead to cardiac arrest.

Typical treatment of such lesions involves the placement of a support structure which holds the artery open to allow for continued blood flow and oxygen supply. The support structure is known as a stent.

Currently-used stents were designed to treat lesions in straight arteries or other bodily vessels. Many lesions, however, occur at bifurcation sites where one artery branches into two arteries. Due to changes in vessel geometry and blood flow characteristics, the bifurcation site is a more complex location to stent compared to a straight vessel. Often, major stent deformations are necessary to adequately cover the target territory at a bifurcation site. This raises concerns regarding optimal treatment using stents such as difficulties in the use of two dedicated stents for the branches after the bifurcation site, stent distortion, which may lead to strut fractures or dislodging of the stent, and an increased risk of periprocedural myocardial infarction [Lesiak, M., 2016, Interv. Cardiol, 11, 2, 124-127].

These issues create a great need for bifurcation stents. These devices must be easy to use, effective in various lesion morphologies, and safe. One such bifurcation stent should be sufficient to stent a side branch at a bifurcation site. Clearly, a straight, tubular stent will not suffice for such a purpose.

In view of the forgoing, one object of the present disclosure is to provide a bifurcation stent for use in a side branch and a method of its use.

SUMMARY OF THE INVENTION

The present disclosure relates to a bifunctional expandable stent delivery assembly, comprising a bifunctional expandable stent comprising a balloon-expandable body portion and a self-expandable trumpet portion, a breakable cover which fits over only the self-expandable trumpet portion but not the balloon-expandable body portion and provides a compressive effect thereby maintaining the self-expandable trumpet portion in a compressed state, and a balloon placed in an interior portion of the bifunctional expandable stent, wherein inflation of the balloon expands the balloon-expandable body portion and expands the self-expandable trumpet portion to a critical diameter at which the breakable cover breaks to allow the self-expandable trumpet portion to self-expand.

In some embodiments, the balloon-expandable body portion has a cylindrical shape constructed of a first metal or metal alloy, and is compressible thereby forming a compressed cylinder having a compressed diameter in the compressed state, expandable thereby forming an expanded cylinder with an expanded diameter which is larger than the compressed diameter in an expanded state, and having a fixed end and a free end, the self-expandable trumpet portion is constructed of a second metal or metal alloy and has a fixed end connected to the proximal end of the balloon-expandable body portion and a free end, the self-expandable trumpet portion is compressible thereby forming a compressed trumpet having a cylindrical shape with a compressed fixed end diameter and a compressed free end diameter, both of which are equal to the compressed diameter of the balloon-expandable body portion in the compressed state, and the self-expandable trumpet portion is expandable, thereby forming an expanded trumpet having a cylindrically-symmetrical flange shape having an expanded fixed end diameter equal to an expanded diameter of the proximal end of the balloon-expandable body portion and an expanded free end diameter greater than the expanded diameter of the proximal end of the balloon-expandable body portion in the expanded state.

In some embodiments, the self-expandable trumpet portion self-expands by a shape-memory effect.

In some embodiments, the first metal or metal alloy is a cobalt-chromium alloy or a platinum-chromium alloy.

In some embodiments, the second metal or metal alloy is a shape-memory alloy.

In some embodiments, the shape-memory alloy is a Nitinol.

In some embodiments, the bifunctional expandable stent further comprises a drug-containing coating.

In some embodiments, the drug-containing coating comprises a polymer and an antiproliferative drug.

In some embodiments, the antiproliferative drug is at least one selected from the group consisting of Everolimus, Zotarolimus, Sirolimus, Biolimus and Umirolimus.

In some embodiments, bifunctional expandable stent delivery assembly further comprises one or more radiopaque markers.

The present disclosure also relates to a method of stenting a patient in need of percutaneous coronary intervention at a bifurcation site, comprising placing into a branch of a bifurcation site the bifunctional expandable stent delivery assembly such that the balloon-expandable body portion is oriented downstream of the bifurcation site and the self-expandable trumpet portion is located at the bifurcation site, and inflating the balloon to the critical diameter, thereby expanding the balloon-expandable body portion and the self-expandable trumpet portion to the critical diameter at which the breakable cover breaks to allow the self-expandable trumpet portion to self-expand.

In some embodiments, the bifurcation site comprises a side branch lesion.

In some embodiments, the bifurcation site has a bifurcation lesion having a Medina classification of (X, Y, 1), where X=0 or 1 and Y=0 or 1.

In some embodiments, the balloon-expandable body portion is oriented in a side branch of the bifurcation site and the self-expandable trumpet portion is located at the carina of the bifurcation site.

In some embodiments, the method further comprises expanding the balloon-expandable body portion and the self-expandable trumpet portion to a diameter less than the critical diameter thereby not breaking the breakable cover and not allowing the self-expandable trumpet portion to self-expand.

BRIEF DESCRIPTION OF THE DRAWINGS

FIGS. 2A-2C are depictions of the bifunctional expandable stent in the expanded state where

FIGS. 3A-3D are depictions of the construction elements and motifs of stent scaffolds, where

FIGS. 4A-4F are depictions of stent scaffold geometry, where

FIGS. 5A-5B show bifurcation site geometry where

DETAILED DESCRIPTION OF THE INVENTION

In the following description, it is understood that other embodiments may be utilized and structural and operational changes may be made without departure from the scope of the present embodiments disclosed herein.

As used herein, the terms "optional" or "optionally" means that the subsequently described event(s) can or cannot occur or the subsequently described component(s) may or may not be present (e.g., 0 wt. %).

As used herein, a "stent" means any device or structure that adds rigidity, expansion force, or support to a prosthesis. Stents typically have a cylindrical frame. For coronary artery stenting, the stent must apply sufficient radial force on the wall of a diseased coronary artery so that the vessel lumen is restored to a near normal diameter whilst subsequently scaffolding the vessel and preventing collapse of the artery in the longer term.

Related to, but distinct from stents are stent grafts. A "stent graft" refers to a prosthesis comprising a stent and a graft material associated therewith that forms a lumen through at least a portion of the length of the stent. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

As used herein, a "catheter" is an apparatus that is connected to a deployment mechanism and houses a medical device that can be delivered over a guidewire. The catheter may include a guidewire lumen for over-the-wire guidance and may be used for delivering a stent or stent graft to a target site. A catheter can have braided metal strands within the catheter wall for structural improvements. The structural elements of the catheter tip can be bonded or laser welded to the braided strands of the catheter to improve the performance characteristics of the catheter tip.

As used herein, a "guidewire" is an elongated cable comprised of various biocompatible materials including metals and polymers. Guidewires may be used for selecting target lumens and guiding catheters to target deployment locations. Guidewires are typically defined as wires used independently of other devices that do not come as part of an assembly.

As used herein, a "balloon" refers to a flexible inflatable container capable of increasing its volume upon inflation with a fluid and decreasing its volume upon deflation.

As used herein, a "bifurcation site" refers to a location in an artery or other bodily vessel where the vessel splits from one parent vessel into two daughter vessels (bifurcates). A bifurcation site comprises a proximal main branch (referring to the parent vessel before or upstream of the bifurcation site), a distal main branch (referring to the larger of the two daughter vessels after or downstream of the bifurcation site), and a side branch (referring to the smaller of the two daughter vessels after or downstream of the bifurcation site).

Figure 1:
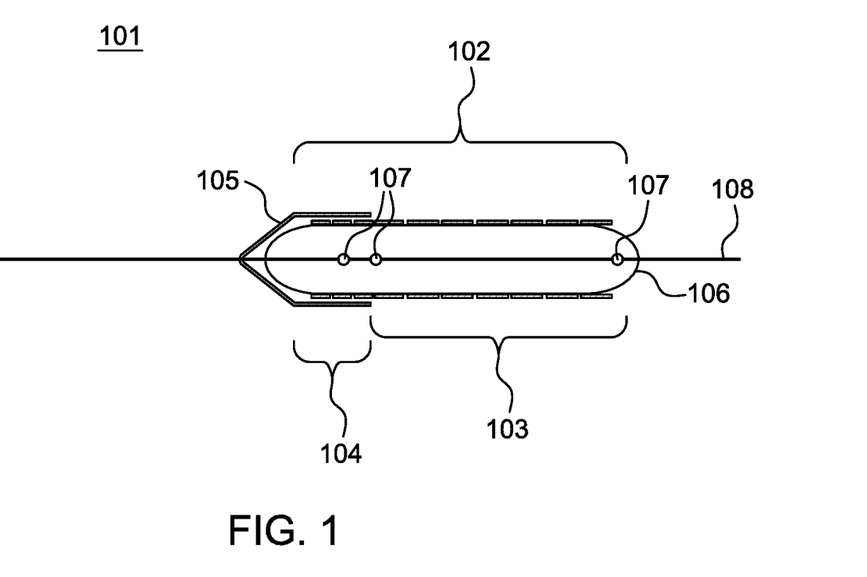
FIG. 1 is a schematic depiction of the bifunctional expandable stent delivery assembly.

According to a first aspect, the present disclosure relates to a bifunctional expandable stent delivery assembly comprising a bifunctional expandable stent, a breakable cover, and a balloon. A depiction of the stent delivery assembly is shown in FIG. 1, with the stent delivery assembly shown with the breakable cover intact and the stent in a compressed state (101). The stent (102) comprises a balloon-expandable body portion (103) and a self-expandable trumpet portion (104). A breakable cover (105) fits over only the self-expandable trumpet portion but not the balloon-expandable body portion and provides a compressive effect thereby maintaining the self-expandable trumpet portion in a compressed state. A balloon (106) is placed in an interior portion of the bifunctional expandable stent, shown prior to inflation in the figure. The stent delivery assembly is depicted in an embodiment where is delivered via catheter or guidewire (108) to facilitate placement. These aspects are described further below.

Figure 2A:
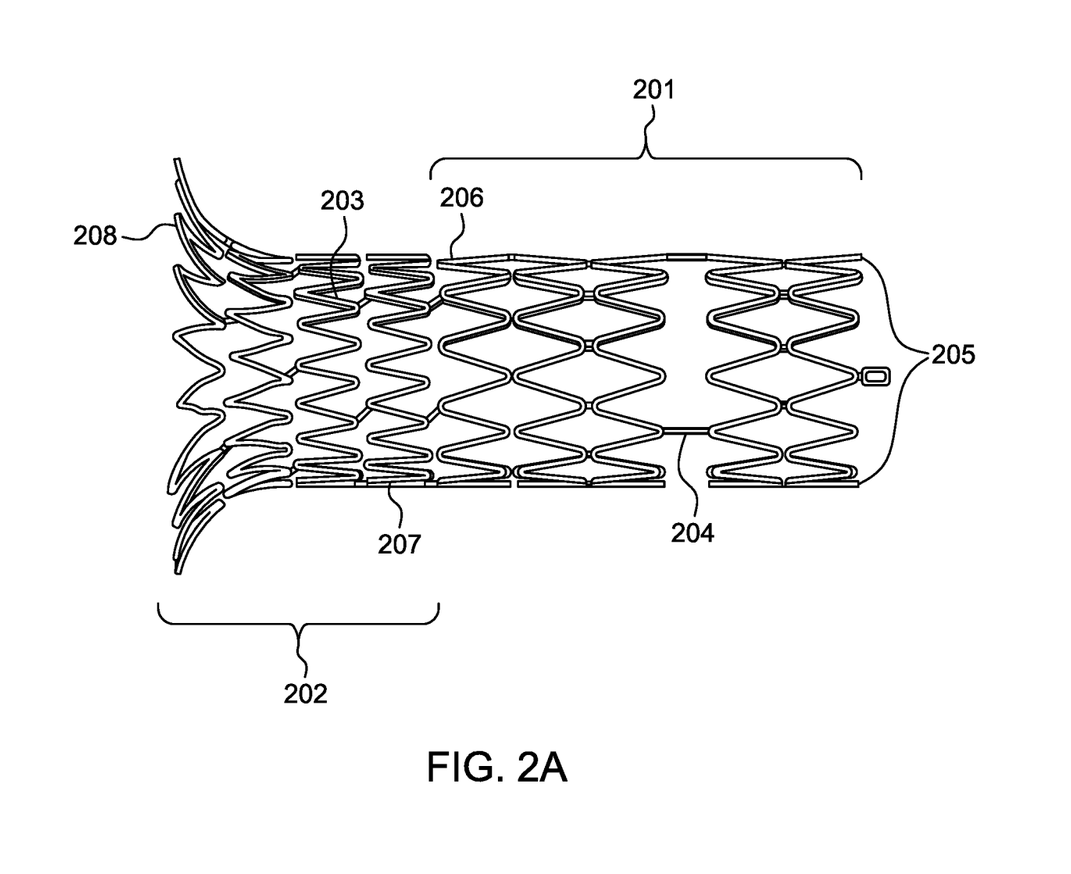
FIG. 2A is a side-view.
Figure 2B:
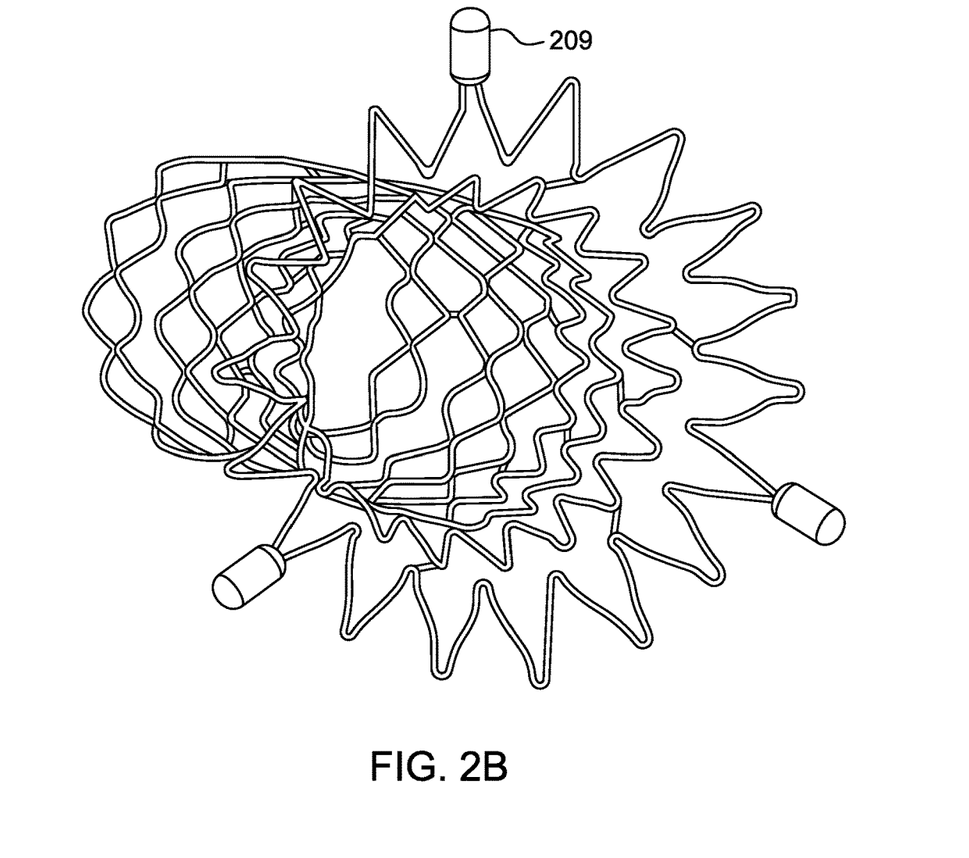
FIG. 2B is a perspective view.

The bifunctional expandable stent comprises a balloon-expandable body portion and a self-expandable trumpet portion. A side view of an exemplary embodiment of the bifunctional expandable stent is shown in FIG. 2A, showing the balloon-expandable body portion (201) and the self-expandable body portion (202). A perspective view of an exemplary embodiment of the bifunctional expandable stent is shown in FIG. 2B. Similar to other stents, the bifunctional expandable stent comprises struts (203) and linkers (204) as described below.

In some embodiments, the balloon-expandable body portion comprises about 5% to about 95% of the overall length of the bifunctional expandable stent, preferably about 10% to about 90%, preferably about 15% to about 85%, preferably about 20% to about 80%, preferably about 25% to about 75%, preferably about 30% to about 70%, preferably about 35 to about 65% of the over all length of the functional expandable stent, the remaining length of the bifunctional expandable stent comprising the self-expandable trumpet portion. In some embodiments, the bifunctional expandable stent has an overall length of 5.0 to 25.0 mm, preferably 5.5 to 24.5 mm, preferably 6.0 to 24.0 mm, preferably 6.5 to 23.5 mm, preferably 7.0 to 23.0 mm, preferably 7.5 to 22.5 mm, preferably 8.0 to 22.0 mm, preferably 8.5 to 21.5 mm, preferably 9.0 to 21.0 mm, preferably 9.5 to 20.5 mm, preferably 10.0 to 20.0 mm, preferably 10.5 to 19.5 mm, preferably 11.0 to 19.0 mm.

In general, both the self-expandable body portion and self-expandable trumpet portion may be constructed of any suitable material known to one of ordinary skill in the art. Stents are generally classified by the material of their construction into two broad categories: metallic stents and polymer stents.

Polymer stents are constructed from polymers, particularly polymers of molecules which are naturally-occurring in the human body. Polymer stents are frequently designed to be degraded and absorbed by or excreted from the body after a period of time. Examples of polymers used to fabricate polymer stents are polylactic acid, tyrosine polycarbonate, and poly salicylic acid/adipic acid. Metallic stents are constructed from metal and metal alloy materials and fall into two categories based upon other materials used in their construction: bare metal stents and polymer coated or drug eluting stents. Polymer coated or drug eluting stents comprise a metal or metal alloy scaffold and a polymer coating, with an optional drug loaded into the polymer coating. Typically, the polymer is a biodegradable or bioabsorbable polymer which is slowly degraded by natural body processes and through the process of being degraded releases the drug into the area and tissue immediately surrounding the stent. For further examples of polymer stents, see Onuma [Onuma, Y., & Serruys, P.W., 2011, Circulation, 123, 779-797, incorporated herein by reference]

Metallic stents are typically categorized based on the method of expansion. Balloon-expandable stents require an expansion force be applied to the stent to expand from a compressed state for delivery and positioning to an expanded state for treating a lesion. This expansion force is typically applied from an interior surface of the balloon-expandable stent by inflation of a balloon placed in an interior portion of the stent. Self-expandable stents, in contrast, do not require an expansion force be applied to the stent. Instead, the stent provides its own expansion force as a property of the material of its construction or its geometry. Metallic balloon-expandable stents and metallic self-expandable stents are typically constructed of different metals or metal alloys. Metallic balloon-expandable stents are commonly constructed from stainless steel, particularly 316L stainless steel. Examples of other materials commonly used for metallic balloon-expandable stents are cobalt-chromium alloys (particularly L605 and MP35N), platinum-chromium alloys (typically proprietary compositions), tantalum, platinum-iridium alloys (such as Pt70/Ir30, Pt75/Ir25 Pt80/Ir20, Pt85/Ir15, Pt90/IR10, and Pt95/Ir5), niobium and niobium alloys (particularly Nb1Zr, Nb28Ta3.5W1.3Zr, and Nb60Ta2Zr), and magnesium alloys (particularly AE21, Mg-2.2Nd-0.1Zn-0.4Zr also known as JDBM, AZ91, AZ31, and WE43). Magnesium alloys are typically chosen for stents designed to be degraded and absorbed by or excreted from the body after a period of time.

Metallic self-expandable stents are commonly constructed from Nitinols (Ni—Ti alloys), Elgiloys (Co—Cr—Ni alloys), and stainless steel. The self-expansion of self-expandable stents may be due to a property of the material the self-expanding stent is comprised of or due to a property of the stent geometry. Self-expanding stents comprising Elgiloys or stainless steel, for example, typically self-expand due to a property of the stent geometry. Alternatively, metallic self-expandable stents are frequently constructed from shape-memory alloys. Shape-memory alloys are named for the ability to "remember" their shape after being plastically deformed. That is, shape-memory alloys, once formed into an original shape, are capable of reverting back to this original shape after being deformed into a final shape, provided the deformation they experience is within a recoverable range. This reversion may be caused by heating or some other external stimulus. The process of deformation and shape recovery can be repeated many times. This property is referred to as the "shape-memory effect". For shape recovery caused by heating, the temperature at which the shape-memory alloy reverts to an original shape may be referred to as the "transition temperature" and is typically dependent upon the composition of the alloy. For metallic self-expandable stents, the transition temperature is typically chosen to be just above or just below normal body temperature (i.e. about 37° C.). Examples of shape-memory alloys are Nitinols (Ni—Ti alloys), Ag—Cd 44/49 at. % Cd, Au—Cd 46.5/50 at. % Cd, Co—Ni—Al alloys, Co—Ni—Ga alloys, Cu—Al—Be—X(X:Zr, B, Cr, Gd) alloys, Cu—Al—Ni 14/14.5 wt. % Al, 3/4.5 wt. % Ni alloys, Cu—Al—Ni—Hf alloys, Cu—Sn approx. 15 at. % Sn alloys, Cu—Zn 38.5/41.5 wt. % Zn alloys, Cu—Zn—X (X=Si, Al, Sn) alloys, Fe—Mn—Si alloys, Fe—Pt approx. 25 at. % Pt alloys, Mn—Cu 5/35 at. % Cu alloys, Ni—Fe—Ga alloys, Ni—Ti approx. 55-60 wt. % Ni alloys, Ni—Ti—Hf alloys, Ni—T—Pd alloys, Ni—Mn—Ga alloys, and Ti—Nb alloys, where at. % refers to atom % an wt. % refers to weight percent. For further examples of metallic stent materials, see Hanawa [Hanawa, T., 2009, Journal of Artificial Organs, 12, 73-79] and Menown [Menown, I.B.A., et. al., 2010, Adv. Ther., 73, 3, incorporated herein by reference].

In the above and below descriptions, it is important to note that the metals used in the name of an alloy do not constitute an exhaustive list of the elemental composition of the alloy. The name of an alloy is typically indicative of the major or most prevalent elements in the alloy. For example a cobalt-chromium alloy must necessarily contain both cobalt and chromium, but may further comprise other elements as well.

In some embodiments, the bifunctional expandable stent is a metallic stent. In some embodiments, the balloon-expandable body portion is constructed of a first metal or metal alloy. In some embodiments, the self-expandable trumpet portion is constructed of a second metal or metal alloy. In some embodiments, the first metal or metal alloy is the same as the second metal or metal alloy. In preferred embodiments, the first metal or metal alloy is not the same as the second metal or metal alloy. In some embodiments, the first metal or metal alloy is selected from the group consisting of stainless steel, cobalt-chromium alloys, platinum-chromium alloys, tantalum, platinum-iridium alloys, niobium, niobium alloys, and magnesium alloys. In preferred embodiments, the first metal or metal alloy is a cobalt-chromium alloy. In alternative preferred embodiments, the first metal or metal alloy is a platinum-chromium alloy. In some embodiments, the self-expandable trumpet portion self-expands due to a property of the material of which it is constructed. In some embodiments, the self-expandable trumpet portion self-expands by a shape-memory effect. In some embodiments, the second metal or metal alloy is a shape-metal alloy. In preferred embodiments, the second metal or metal alloy is a Nitinol.

Both the balloon-expandable body portion and the self-expandable trumpet portion are compressible, i.e. capable of existing in a compressed state and an expanded state. It is in the compressed state that the stent is envisioned as a component of the bifunctional expandable stent delivery assembly of the current disclosure. It is further envisioned that the expanded state is the configuration in which the stent exists in a patient after delivery. In the compressed state, the balloon-expandable body portion takes the form of a compressed cylinder having a compressed diameter. In the expanded state, the balloon-expandable body portion takes the form of a cylinder having an expanded diameter (see FIG. 2A). The expanded diameter is larger than the compressed diameter. The balloon-expandable body portion has a proximal end (205) and a distal end (206). The self-expandable trumpet portion is attached to the proximal end of the cylindrical balloon-expandable body portion. The end of the balloon-expandable body portion which is not connected to the self-expandable trumpet portion is referred to as the "distal end" (206). The end of the self-expandable trumpet portion which is attached to the balloon-expandable body portion is referred to as the "fixed end" (207). The other end of the self-expandable trumpet portion (i.e. the end not attached to the balloon-expandable body portion) is referred to as the "free end" (208). In the compressed state, the self-expandable body portion takes the form of a compressed trumpet. The compressed trumpet has a cylindrical shape in which the compressed free end diameter is approximately equal to the compressed fixed end diameter (see FIG. 2A). In preferred embodiments, the compressed fixed end diameter and the compressed free end diameter are equal to the compressed diameter of the balloon-expandable body portion. Such a configuration gives the compressed stent an overall cylindrical shape. In the expanded state, the self-expandable trumpet portion has a trumpet shape. The trumpet shape refers to a cylindrically symmetrical shape where the ends of the shape have different diameters, the shape gradually and smoothly flaring from a smaller diameter to a larger diameter. The trumpet shape may alternatively be thought of as nominally cylindrical with a flared, cone-shaped or flange-shaped end. The trumpet shape is preferably free of abrupt or sharp-edged transitions or changes in diameter. Instead, an exterior surface of the trumpet preferably shows a smooth, continuous transition from a narrow end to a flared end. In the expanded state, the self-expandable trumpet portion has an expanded free end diameter and an expanded fixed end diameter, the fixed proximal end diameter being smaller than the expanded free end diameter. In preferred embodiments, the expanded fixed end diameter is nominally equal to the expanded diameter of the proximal end of the balloon-expandable body portion. In some embodiments, the balloon-expandable body portion is in the form of a tapered cylinder. The tapered cylinder has a non-uniform diameter along the length of the cylinder (i.e. the diameter of the tapered cylinder changes along its length). Such a tapered cylinder may have a larger proximal end expanded diameter or a larger distal end expanded diameter. In such embodiments, the tapered cylinder has a diameter profile in which the tapered cylinder has a proximal end expanded diameter portion, a taper portion, and a distal end expanded diameter portion. In such embodiments, the proximal end expanded diameter portion and the distal end expanded diameter portion each have a diameter which is constant along the length of the portion. In such embodiments, the taper portion has a non-constant diameter along the length of the portion in which a smooth and continuous change in diameter from a diameter equal to the proximal end expanded diameter to the distal end expanded diameter occurs moving along the length of the taper portion in a direction from the proximal end portion to the distal end portion. In some embodiments, the proximal end diameter portion and taper portion together comprise less than 50%, preferably less than 45%, preferably less than 40%, preferably less than 35%, preferably less than 30%, preferably less than 25%, preferably less than 20%, preferably less than 15%, preferably less than 10% of the overall length of the tapered cylinder. This tapered cylinder allows for the use of appropriately sized balloon-expandable body portions and self-expandable trumpet portion which may have different nominal sizes so as to better fit a bifurcation site having a main branch and a side branch of different diameters.

In some embodiments, the expanded diameter of the balloon-expandable body portion is 1.0 to 5.0 mm, preferably 1.1 to 4.9 mm, preferably 1.2 to 4.8 mm, preferably 1.3 to 4.7 mm, preferably 1.4 to 4.6 mm, preferably 1.5 to 4.5 mm, preferably 1.6 to 4.4 mm, preferably 1.7 to 4.3 mm, preferably 1.8 to 4.2 mm, preferably 1.9 to 4.1 mm, preferably 2.0 to 4.0 mm, preferably 2.05 to 3.95 mm, preferably 2.10 to 3.90 mm, preferably 2.15 to 3.85 mm, preferably 2.20 to 3.80 mm, preferably 2.25 to 3.75 mm, preferably 2.30 to 3.70 mm, preferably 2.35 to 3.65 mm, preferably 2.40 to 3.60 mm, preferably 2.425 mm to 3.575 mm, preferably 2.45 to 3.55 mm, preferably 2.475 to 3.535 mm, preferably 2.50 to 3.50 mm.

Figure 2C:
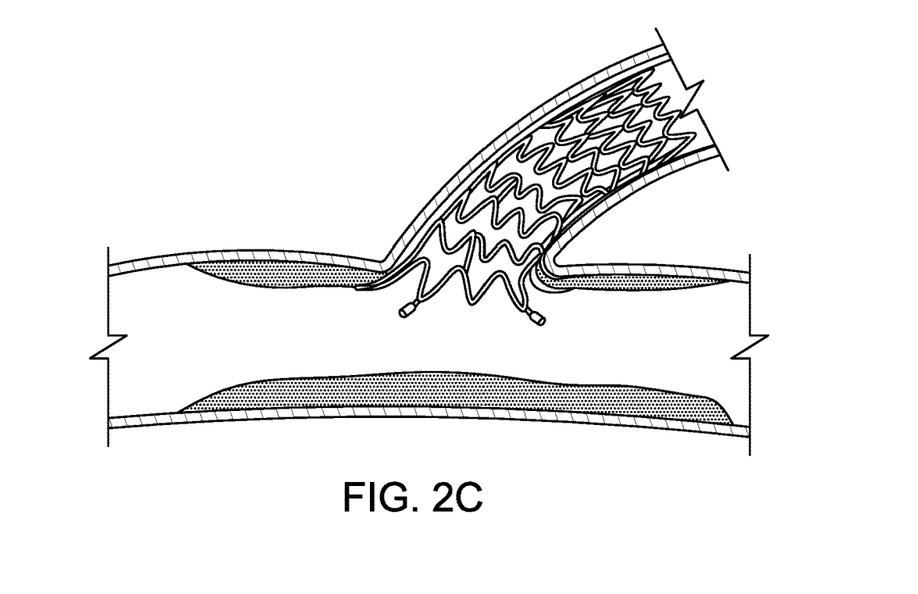
FIG. 2C is a view showing the bifunctional expandable stent deployed in a bifurcation site.

In some embodiments, the above description of various diameters refers to unconstrained diameters in which the stent is deployed (i.e. expanded and released from a catheter or guidewire) outside of an artery or other bodily vessel. In some embodiments, the expanded cylinder may have slight deviations in diameter along the length of the expanded cylinder so as to fit or conform to natural changes in the diameter of the artery or other bodily vessel. In such embodiments, the slight deviations are less than 10%, preferably less than 9%, preferably less than 8%, preferably less than 7%, preferably less than 6%, preferably less than 5%, preferably less than 4%, preferably less than 3%, preferably less than 2%, preferably less than 1% of a mean diameter of the expanded cylinder. In some embodiments, the above description of the expanded cylinder refers to a situation in which the stent is deployed outside of an artery or other bodily vessel. In some embodiments, the expanded cylinder bends along a length of the expanded cylinder so as to fit or conform to a natural curvature of an artery or other bodily vessel. In some embodiments, the above description of the shape of the trumpet shape refers to a situation in which the stent is deployed outside of an artery or other bodily vessel. In some embodiments, the trumpet shape may deviate from perfect cylindrical symmetry, for example by bending, so as to fit or conform to a natural shape or curvature of a bifurcation site. Such deviation may be advantageous in securely anchoring the stent in the bifurcation site. Such deviation may be of particular advantage in bifurcation sites which do not have a "T-shape" in which the angles between the proximal main branch and side branch and the distal main branch and side branch are not equal to about 90°. Both FIG. 2A and FIG. 2B depict exemplary embodiments of the bifunctional expandable stent in an unconstrained expanded state. An example of deviations from the geometry depicted in FIGS. 2A and 2B caused by deployment of the bifunctional expandable stent into an artery or other bodily vessel is shown in FIG. 2C. Here, the bifunctional expandable stent is shown with a slight curvature along a longitudinal axis (i.e. a direction oriented along a length of the stent running in a direction from the distal end of the self-expandable trumpet portion to the balloon-expandable body portion) to better fit or conform to a natural curvature of the artery or other bodily vessel.

In some embodiments, the bifunctional expandable stent further comprises anchor portions. The anchor portions may be projections, enlarged struts, barbs, flaps, or other shapes. These anchor portions further secure the bifunctional expandable stent into a bifurcation site. This further securing may be accomplished by various mechanisms including, but not limited to the anchoring portions increasing friction between the bifunctional expandable stent and the artery or other bodily vessel, the anchoring portions increasing a flexural stiffness of the self-expandable trumpet portion, and the anchoring portions piercing the artery or other bodily vessel. In some embodiments, the anchoring portions are located at, disposed upon, or attached to the free end of the self-expandable trumpet portion. An example of such an embodiment is shown in FIG. 2B, showing the anchoring portions (209) as flattened, enlarged struts. In some embodiments, the anchoring portions are located at, disposed upon, or attached to the distal end of the balloon-expandable body portion. For other examples of anchoring portions, see US20180228626 A1, incorporated herein by reference].

In some embodiments, the bifunctional expandable stent further comprises drug-containing coating. In such embodiments, the bifunctional expandable stent may be considered a drug-eluting stent as described above. In such embodiments, the drug-containing coating comprises a polymer and an antiproliferative drug. In general, any suitable polymer may be used that is known to one of ordinary skill in the art. In some embodiments, the polymer is a biodegradable or bioresorbable polymer. Examples of biodegradable or bioresorbable polymers used for drug-eluting stents are polylactic acid (PLA), poly(lactic acid-co-glycolic acid) (PLGA), acid polycaprolactone, tyrosine polycarbonate, and poly salicylic acid/adipic acid. In alternative embodiments, the polymer is a durable polymer. A durable polymer refers to a polymer which is not degraded and absorbed by or excreted from the body by natural body processes. Examples of durable polymers used for drug-eluting stents are polyvinylidenedifluoride (PVDF), PBMA (poly-n-butylmethacrylate), polyethylene-co-vinyl-acetate (PEVA), poly(styrene-b-isobutylene-b-styrene) block copolymer, and polytetrafluoroethylene (PTFE) or expanded polytetrafluoroethylene (ePTFE). In some embodiments, the antiproliferative drug is at least one selected from the group consisting of everolimus, zotarolimus, sirolimus, biolimus and umirolimus.

Stents are typically composed of a scaffold or scaffolding that includes a pattern or network of interconnecting structural elements formed from wires, filaments, tubes, ribbons or sheets of material rolled into a cylindrical shape. This scaffold gets its name because it physically holds open and, if desired, expands the wall of a passageway (e.g. artery) in a patient. Typically, stents are capable of being compressed or crimped onto a delivery assembly so that they can be delivered to and deployed at a treatment site. Delivery and deployment is typically performed with a catheter.

A stent scaffold may be fabricated from a single piece of wire, filament, or tubing which is bent, wound, folded and/or woven into a desired framework shape. The single piece may additionally be welded, crimped, or tied at one or more places along the length of the single piece. Such welds, crimps, or ties may serve various functions, such as increasing radial stiffness, increasing longitudinal stiffness, decreasing separation of portions of the single piece during bending, and securing the ends of the single piece. Such stents are known as single wire stents, continuous wire stents, sinusoidal continuous wire stents, or woven stents. An alternative stent scaffold fabrication method is the cut slotted tube type. The cut slotted tube type scaffold fabrication method typically involves a single sheet or tube of material from which portions are removed to create the stent scaffold. These portions may be removed by stamping, mechanical cutting, laser cutting, or similar technique. If beginning from a sheet of material, the sheet is then rolled and secured into a cylindrical shape. A third stent scaffold fabrication method is the multilink method, in which many pieces of wire, filament, or tubing are interlinked to form the stent scaffold. The interlinking is typically achieved by welding, crimping, tying, or weaving. A fourth stent fabrication method is 3D printing.

Figure 3A:
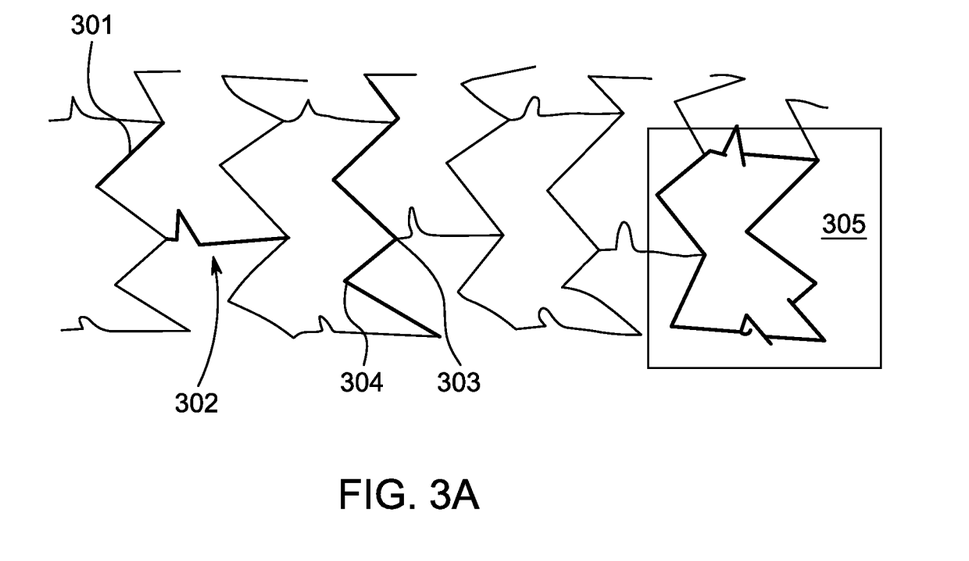
FIG. 3A shows the basic elements of a stent scaffold.
Figure 3B:
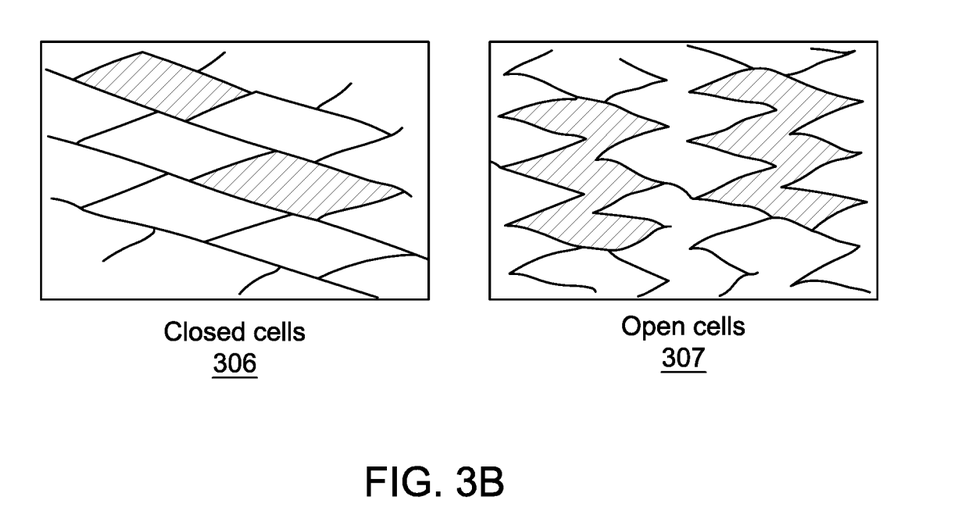
FIG. 3B shows a comparison of open cells and closed cells.
Figure 3C:
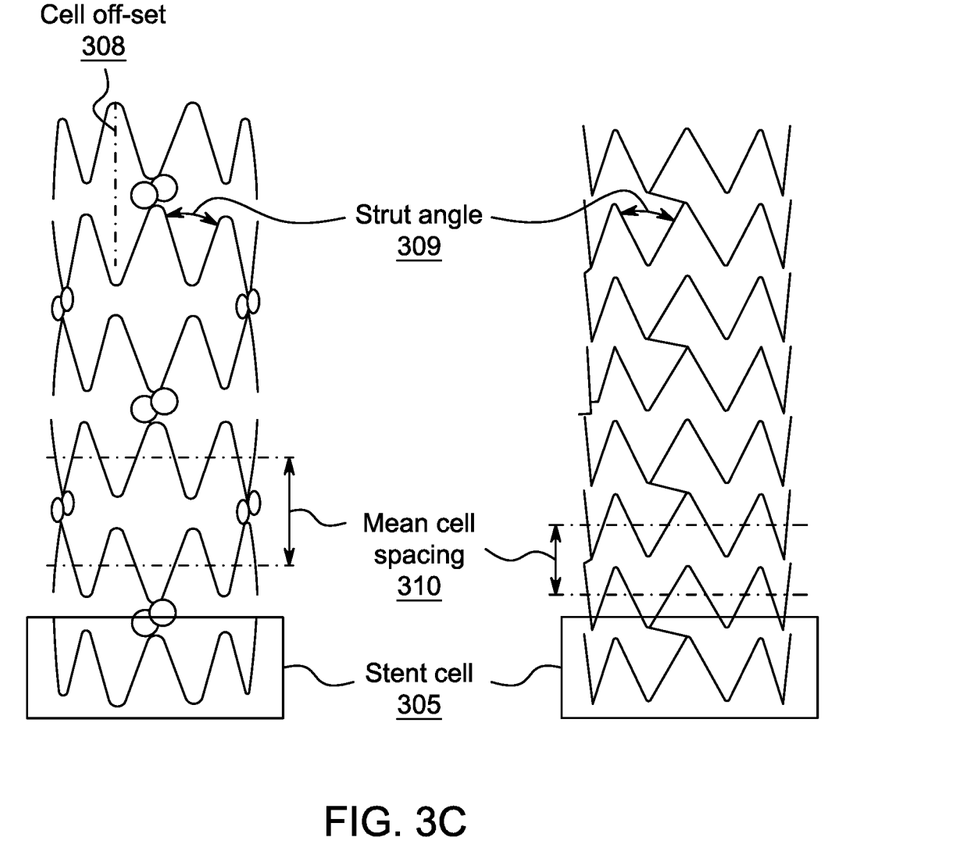
FIG. 3C shows stent cell connection parameters.
Figure 3D:
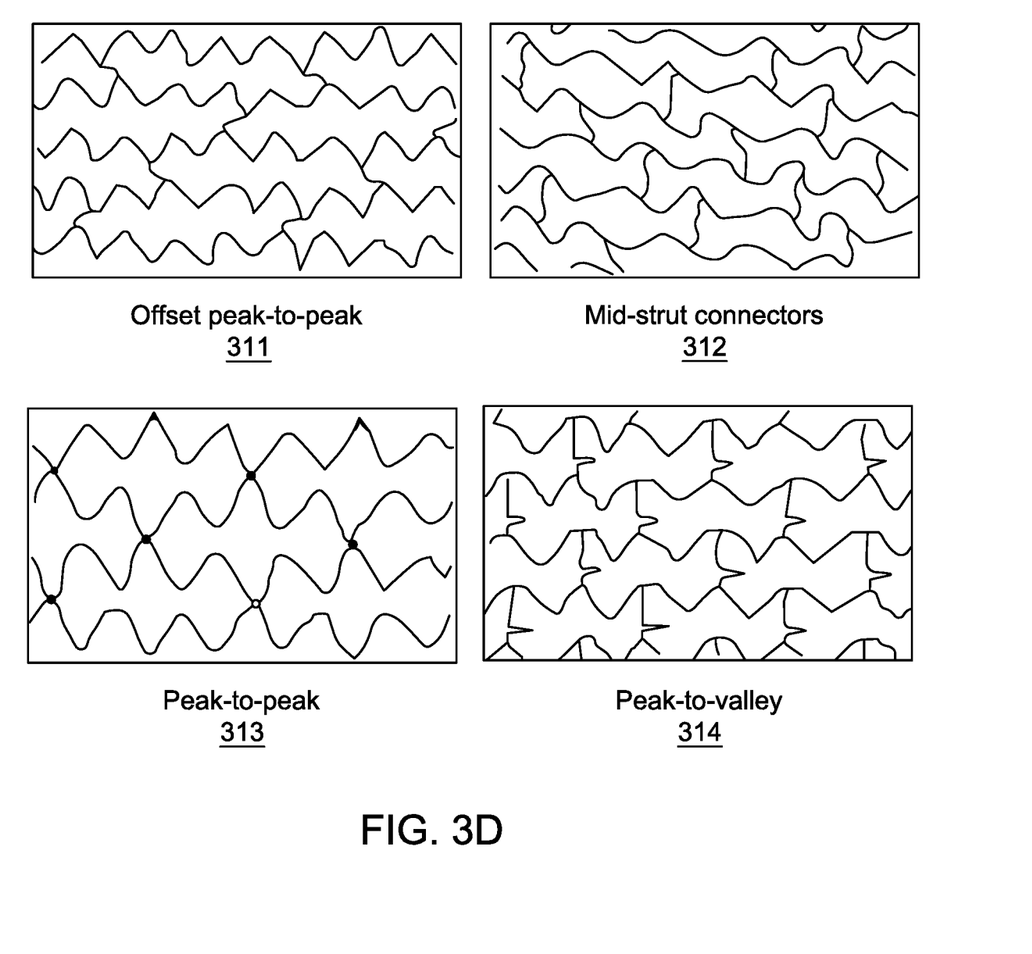
FIG. 3D shows examples of stent cell connection motifs.
Figure 4A:
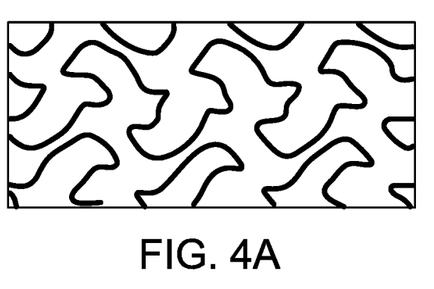
FIG. 4A is an open-cell, curved strut, point connector geometry.
Figure 4B:
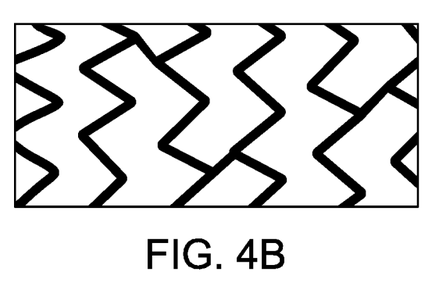
FIG. 4B is an open-cell, straight strut, straight connector geometry.
Figure 4C:
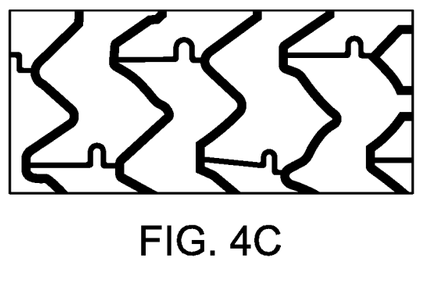
FIG. 4C is an open-cell, curved strut, curved connector geometry.
Figure 4D:
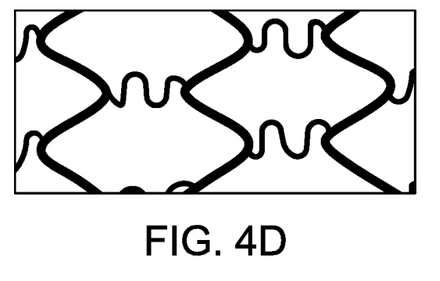
FIG. 4D is a close-cell, straight strut, curved connector geometry.
Figure 4E:
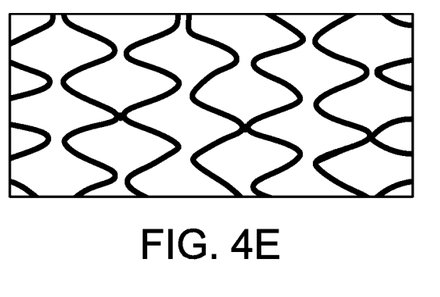
FIG. 4E is an open-cell, straight strut, point connector geometry.
Figure 4F:
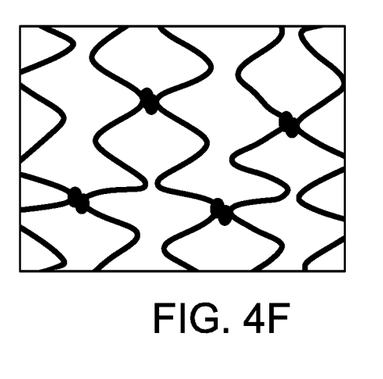
FIG. 4F is an open-cell, straight strut, curved connector geometry.

The geometry of a stent scaffold can determine the properties of the stent, such as radial stiffness, longitudinal stiffness, and restenosis resistance. Typically, the stent scaffold comprises structural elements which are connected in various motifs to make up the stent geometry. A depiction of these structural elements is shown in FIG. 3A, which depicts struts (301), connectors (302), peaks (303), and valleys (304), which make the basic structural unit of the stent scaffold, the cell (305) and connect cells to each other. The struts may be straight or curved. Two types of cells are commonly-used in stent scaffolds, defined by the orientation of struts which make up the cells. The two types of cells are depicted in FIG. 3B, showing closed cells (306) and open cells (307). Closed cells are cells in which struts are only joined on cell vertices which are oriented toward the exterior of the cell while open cells have struts which are joined on vertices, some of which are oriented toward the interior of the cell. Alternatively, in closed cells, all internal inflection points of the struts are connected by connectors to adjacent cells, while open cells have internal inflection points of the struts which are not connected by connectors to adjacent cells. Open cells are typically more flexible and capable of expanding to a greater extent than closed cells. The cells, whether open or closed, are connected by connectors, which may be point connectors or non-point connectors which may be straight or curved similar to struts. In addition to the cell geometry, the stent scaffold geometry is further defined by the geometry of the cell-to-cell connections. Shown in FIG. 3C are some of the factors of the cell-to-cell connections such as the cell offset (308), strut angle (309), and mean cell spacing (310). Connections between cells may be made by a variety of motifs, examples of which are shown in FIG. 3D, which shows off-set peak-to-peak (311), mid-strut connectors (312), peak-to-peak (313), and peak-to-valley (314). Combinations of strut geometry, cell type, connector geometry, and cell-to-cell connection motif give rise to many different stent scaffold geometries. Examples of some of the available stent scaffold geometries are shown in FIGS. 4A-4F. For further examples of stent scaffold geometry, see Stoeckel, et. al. [Stoeckel, et. al., 2002, Min Invas Ther & Allied Technol., 11, 4, 137-147, incorporated herein by reference], Tomberli, B., et. al. [Tomberli, et. al., 2018, Rev. Esp. Cardiol, 71, 5, 312-319], and Noad, et. al. [Noad, R. L., et. al., 2014, Interv. Cardiol., 9, 2, 89-93, incorporated herein by reference]. In general, the bifunctional expandable stent may have any suitable stent scaffold geometry known to one of ordinary skill in the art. In some embodiments, the bifunctional expandable stent comprises straight struts. In alternative embodiments, the bifunctional expandable stent comprises curved struts. In some embodiments, the bifunctional expandable stent comprises both straight struts and curved struts. In some embodiments, the bifunctional expandable stent comprises open cells. In alternative embodiments, the bifunctional expandable stent comprises closed cells. In some embodiments, the bifunctional expandable stent comprises both open cells and closed cells. In some embodiments, the bifunctional expandable stent comprises point connectors. In some embodiments, the bifunctional expandable stent comprises straight non-point connectors. In some embodiments, the bifunctional expandable stent comprises curved non-point connectors. In some embodiments, the bifunctional expandable stent comprises both straight and curved non-point connectors. In some embodiments, the bifunctional expandable stent comprises both point and non-point connectors. In such embodiments, the non-point connectors may be straight, curved, or both. In some embodiments, the bifunctional expandable stent comprises peak-to-peak connections. In some embodiments, the bifunctional expandable stent comprises off-set peak-to-peak connections. In some embodiments, the bifunctional expandable stent comprises peak-to-valley connections. In some embodiments, the bifunctional expandable stent comprises mid-strut co connections. In some embodiments, the bifunctional expandable stent comprises more than one type of connection as described above. In preferred embodiments, the bifunctional expandable stent has an open-cell, straight strut, point connection geometry. An example of such a preferred geometry is shown in FIG. 4E.

The breakable cover fits over only the self-expandable trumpet portion but not the balloon-expandable body portion. The breakable cover provides a compressive effect thereby maintaining the self-expandable trumpet portion in a compressed state. In some embodiments, removal of the compressive effect provided by the breakable cover, for example by breaking and removing of the breakable cover, allows the self-expandable trumpet portion to self-expand. The breakable cover may be constructed of any suitable material known to one of ordinary skill in the art. Examples of such suitable materials include polymers and metals as described above. The breakable cover is broken by inflation of the balloon and subsequent expansion of the balloon-expandable body portion. Upon inflation of the balloon and expansion of the balloon-expandable body portion beyond a critical diameter, the breakable cover breaks, thereby allowing the self-expandable trumpet portion to self-expand. In some embodiments, the breakable cover is configured to be maintained at the critical diameter, such that any expansion or inflation of the balloon causes the breakable cover to break. In alternative embodiments, the breakable cover is maintained at a diameter below the critical diameter (a sub-critical diameter). In such embodiments, the breakable cover is able to expand to the critical diameter, beyond which it breaks. In such embodiments, the breakable cover is able to reversibly expand from the sub-critical diameter to the critical diameter (but not beyond) and back.

In some embodiments, the breakable cover fits over the entirety of the self-expandable trumpet portion. In some embodiments, the breakable cover fits over the entirety of the self-expandable trumpet portion with a small extension (1-2 mm) over the balloon expandable portion. In such embodiments, the breakable cover has a length equal to the self-expandable trumpet portion. In alternative embodiments, the breakable cover does not fit over the entirety of the self-expandable trumpet portion. In general, the breakable cover fits over a sufficient portion of the self-expandable trumpet portion to provide sufficient compressive force to maintain the self-expandable trumpet portion in the compressed state. In some embodiments, the breakable cover fits over at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75% of the self-expandable trumpet portion. In such embodiments, the breakable cover is positioned such that the free end of the self-expandable trumpet portion is covered by the breakable cover. In such embodiments, the portion of the self-expandable trumpet portion not covered by the breakable cover extends from the breakable cover to the fixed end of the self-expandable trumpet portion.

In some embodiments, the breakable cover has an inner diameter which is about equal to an outer diameter of the self-expandable trumpet portion in a compressed state. In such embodiments, an inner surface of the breakable cover is in contact with an outer surface of the bifunctional expandable stent in the compressed state. In some embodiments, the breakable cover has an outer diameter which is greater than an outer diameter of the bifunctional expandable stent. In some embodiments, the breakable cover has an outer diameter which is smaller than an inner diameter of a retractable sheath which is part of the catheter or guidewire the bifunctional expandable stent delivery assembly is attached to or disposed upon. In some embodiments, the breakable cover has a capped-cylindrical shape. The capped cylindrical shape comprises a cylindrical body with a cap portion. The cap portion may be flat, pointed, rounded, conical, or some other shape. In such embodiments, the cap portion is oriented to cover the free end of the self-expandable trumpet portion. In some embodiments, the breakable cover has a tapered-capped-cylindrical shape. The tapered-capped-cylindrical shape comprises a tapered cylinder body as described above and a cap portion as described above. In such embodiments, the tapered cylinder body is tapered such that the tapered cylinder has a larger diameter near the cap portion which decreases moving along the length of the cylinder in a direction away from the cap portion.

In general the breakable cover may be constructed of any suitable material known to one of ordinary skill in the art. In some embodiments, the breakable cover is constructed of a polymer. In some embodiments, the polymer is a durable polymer as described above. In alternative embodiments, the polymer is a biodegradable or bioresorbable polymer as described above. In some embodiments, the breakable cover comprises breaking facilitating structures. These breaking facilitating structures are elements of the structure of the breakable cover which facilitate breaking. Examples of the method by which these breaking facilitating structure facilitate breaking include a reduction of the magnitude of a breaking force or the introduction of a breakable cover expansion force. In order for the breakable cover to break, a breaking force of sufficient force must be supplied that breaks the breakable cover when it exceeds the critical diameter. In some embodiments, the breaking force is provided by the inflation of the balloon. In some embodiments, the reduction of the magnitude of the breaking force is accomplished by thinning, scoring, and/or perforating the breakable cover. The thinning, scoring, and/or perforating preferably creates thinned, scored, and/or perforated sections of the breakable cover which have a lower measure of mechanical strength or integrity (such as fracture toughness) compared to sections of the breakable cover which are not thinned, scored, or perforated. In some embodiments, fractures may initiate in sections which are thinned, scored, and/or perforated. In such embodiments the fractures may propagate through the sections which are thinned, scored, and/or perforated preferentially compared to sections which are not thinned, scored, and/or perforated. In some embodiments, the breakable cover breaks, but remains one continuous piece. In alternative embodiments, the breakable cover breaks into two or more pieces.

In some embodiments, the breakable cover is permanently attached to the bifunctional expandable stent. In such embodiments, the breakable cover remains attached to the bifunctional expandable stent when the bifunctional expandable stent is in an expanded state. Such embodiments prevent the breakable cover from entering the blood stream.

In some embodiments, the breakable cover is released from the bifunctional expandable stent during stent deployment. In such embodiments, the breakable cover may be retrieved after stent deployment.

The breakable cover, once broken, may be temporarily held by the bifunctional expandable stent so as to not enter the blood stream. In such embodiments, the breakable cover may be retrieved and removed from the body by any suitable method or with any suitable device known to one of ordinary skill in the art, such as a laparoscopic tool or catheter.

In alternative embodiments, the breakable cover is not retrieved after stent deployment. In such embodiments, the breakable cover is biodegraded or bioresorbed. In such embodiments, the breakable cover is constructed of a biodegradable or bioresorbable polymer as described above.

Alternatively, the breakable cover may be attached to a catheter or guidewire that the bifunctional stent delivery assembly is attached to or disposed upon. In such embodiments, the breakable cover, once broken, is removed by an action of removing the catheter or guidewire.

In some embodiments, the balloon is placed in an interior portion of the bifunctional expandable stent. In general, the balloon may be any suitable balloon known to one of ordinary skill in the art. Examples of suitable materials for constructing the balloon are PVC polyvinyl chloride (PVC), cross-linked polyethylene, polyethylene terephthalate (PET), and nylon.

In some embodiments, the balloon is integrated into a catheter. Such a device is known as a "balloon catheter". In such embodiments, the bifunctional expandable stent and breakable cover are attached to, placed around, or disposed upon the balloon to create the bifunctional expandable stent delivery assembly. For examples of balloon catheters, see U.S. Pat. No. 5,383,853A, incorporated herein by reference and/or U.S. Pat. No. 9,061,126B2, incorporated herein by reference.

In some embodiments, the balloon is attached to a guidewire. In such embodiments, the guidewire serves to position the delivery assembly. In such embodiments, inflation of the balloon is performed by a separate inflation apparatus, such as an inflation tube, inflation wire, or inflation catheter. In some embodiments, the balloon reversibly attaches to a catheter or guidewire. In such embodiments, the entire delivery assembly may be assembled prior to attaching to said catheter or guidewire.

In some embodiments, the bifunctional expandable stent delivery assembly further comprises one or more radiopaque markers. Radiopaque markers are metallic structures comprising high atomic number (high-Z) metals which are visible by medical diagnostic techniques such as X-ray imaging or CAT scans. Examples of commonly-used high atomic number metals are tantalum, gold, palladium, platinum, iridium, and mixtures thereof. In some embodiments, the radiopaque markers take the form of bands or rings. In alternative embodiments, the radiopaque markers take the form of discs. In some embodiments, the radiopaque markers are integrated into or attached to the bifunctional expandable stent. In alternative embodiments, the radiopaque markers are integrated into or attached to a catheter or guidewire to which the bifunctional expandable stent delivery assembly is attached. Such an embodiment is shown in FIG. 1, with the radiopaque markers (107) being in the form of bands placed on the delivery guidewire (108). For examples of radiopaque markers, see U.S. Pat. No. 9,693,885B2 and U.S. Pat. No.6,334,871B1.

The present disclosure also relates to a method of stenting a patient in need of percutaneous coronary intervention at a bifurcation site, comprising placing into a branch of a bifurcation site the bifunctional expandable stent delivery assembly described above such that the balloon-expandable body portion is oriented downstream of the bifurcation site and the self-expandable trumpet portion is located at the bifurcation site and inflating the balloon to the critical diameter, thereby expanding the balloon-expandable body portion and the self-expandable trumpet portion to the critical diameter at which the breakable cover breaks to allow the self-expandable trumpet portion to self-expand.

Figure 5A:
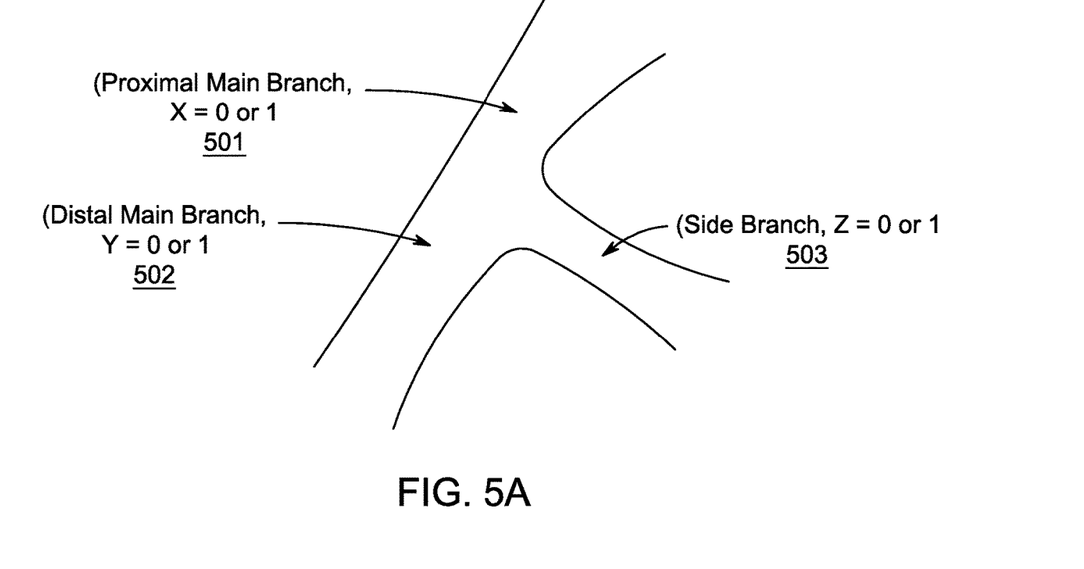
FIG. 5A shows bifurcation site areas and FIG. 5B is a depiction of the Medina Classification for bifurcation lesions.
Figure 5B:
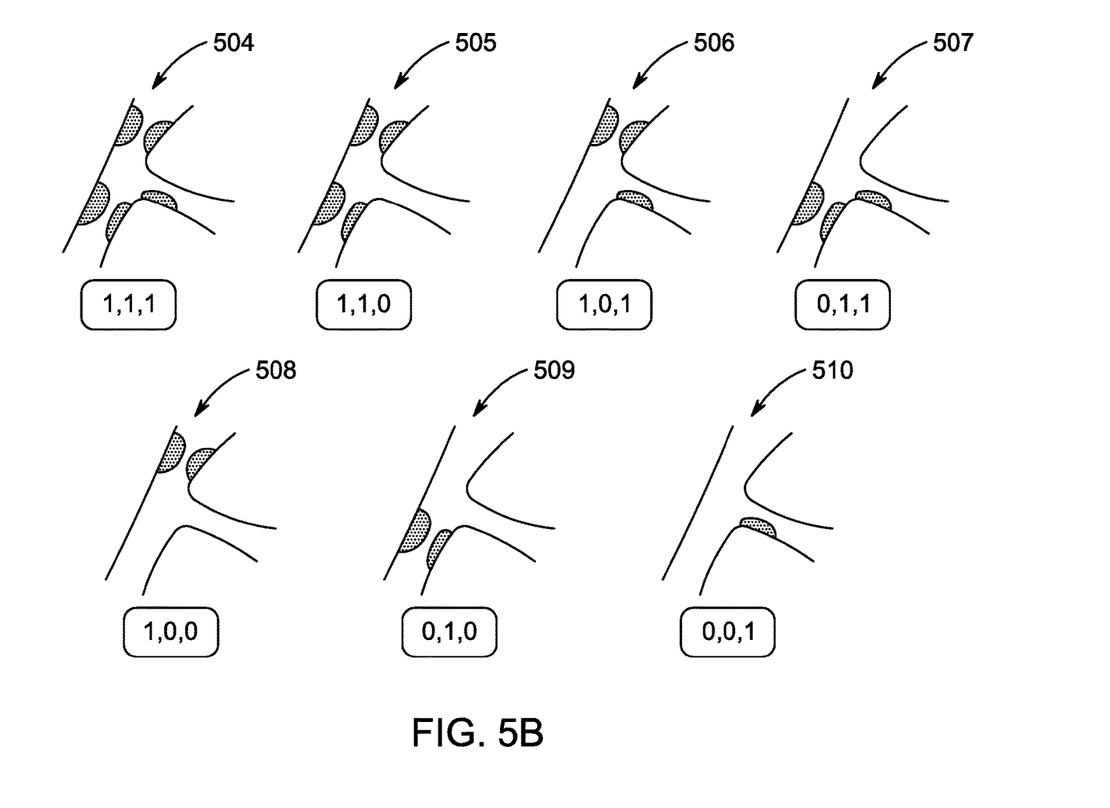

A bifurcation site in need of stenting is typically classified based on the location of one or more lesions or areas that must be covered by the stent or stents. One such classification scheme is the Medina Classification. An overview of the Medina Classification is shown in FIG. 5A. The Medina Classification uses a nomenclature (X, Y, Z), where X=0 or 1, Y=0 or 1, and Z=0 or 1 based on the presence (1) or absence (0) of a lesion or area that must be covered by the stent in three locations associated with the bifurcation. The proximal main branch is designated with the X variable (501), the distal main branch is designated with the Y variable (502), and the side branch is designated with the Z variable (503). This leads to 7 possible Medina Classifications, which are shown in FIG. 5B. the (1,1,1) classification (504) shows lesions in all three areas. The (1,1,0) classification (505) shows lesions in the proximal and distal main branches but not in the side branch. The (1,0,1) classification (506) shows lesions in the proximal main branch and side branch but not in the distal main branch. The (0,1,1) classification (507) shows lesions in the distal main branch and side branch but not in the proximal main branch. The (1,0,0) classification (508) shows only a lesion in the proximal main branch. The (0,1,0) classification (509) shows only a lesion in the distal main branch. The (0,0,1) classification (510) shows only a lesion in the side branch.

Figure 6:
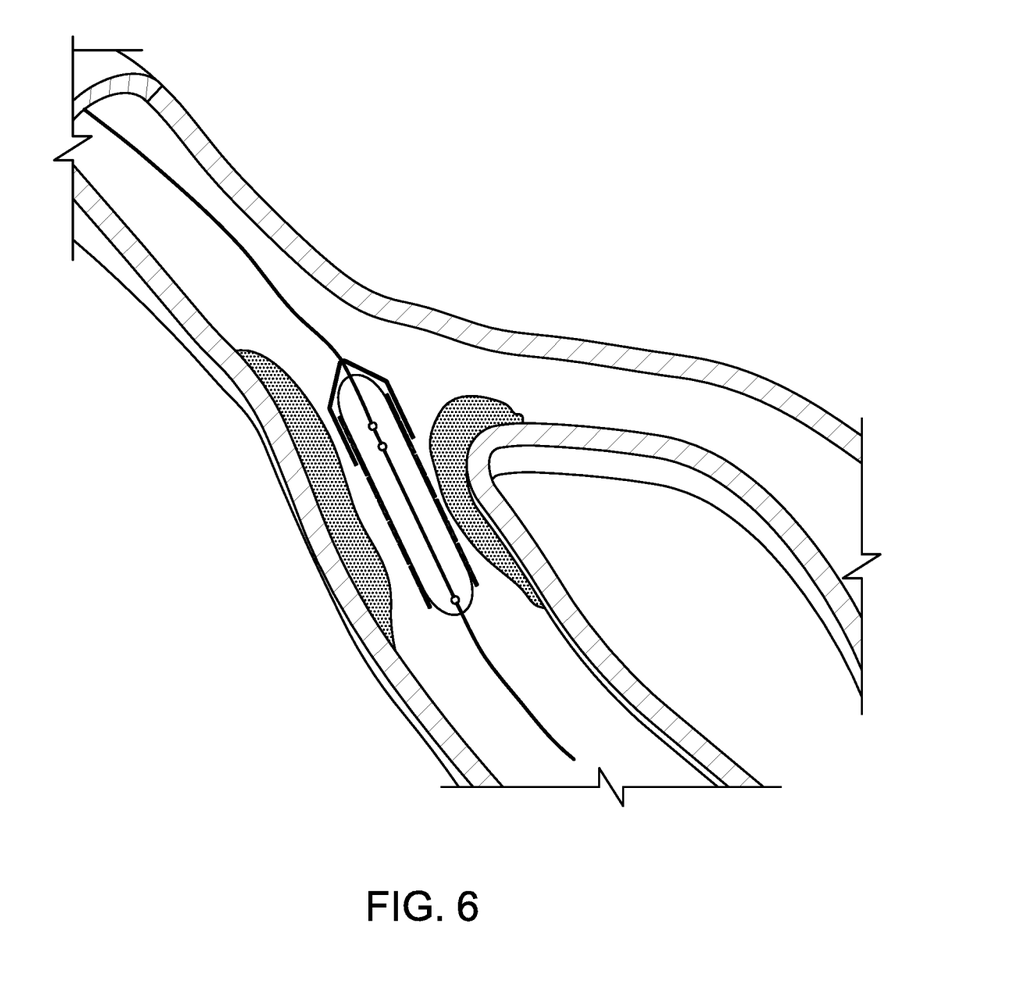
FIG. 6 is a depiction of the method for stenting in a bifurcation site.

In preferred embodiments, the method treats bifurcation sites comprising a side branch lesion. In preferred embodiments, the bifurcation site has a bifurcation lesion having a Medina Classification of (X, Y, 1), where X=0 or 1 and Y=0 or 1. In such embodiments, the balloon-expandable body portion is oriented in a side branch of the bifurcation site and the self-expandable trumpet portion is located at the carina of the bifurcation site. The carina of a bifurcation site is the inflection point where the bifurcation occurs (i.e. where the parent branch splits into the two daughter branches). A depiction of such an orientation before balloon inflation and stent deployment is shown in FIG. 6, while FIG. 2C depicts an exemplary embodiment of the orientation after balloon inflation and stent deployment.

In general, any suitable method of placing the bifunctional stent delivery assembly known to one of ordinary skill in the art may be used. In preferred embodiments, the placing is accomplished with a catheter as described above.

In some embodiments, the method further comprises placing a second stent which is oriented from the proximal main branch to the distal main branch. In some embodiments, the second stent may be any stent known to one of ordinary skill in the art. In some embodiments, the bifunctional expandable stent is placed into the side branch as described above. In some embodiments, the second stent may be placed by any suitable method or technique known to one of ordinary skill in the art. In some embodiments, the second stent may be placed before or after the placement of the bifunctional expandable stent into the side branch. In some embodiments, the bifunctional expandable stent is not connected to the second stent. In alternative embodiments, the bifunctional expandable stent is connected to the second stent. In such embodiments, the bifunctional expandable stent may be connected to the second stent by any suitable method or technique known to one of ordinary skill in the art. Examples of such methods or techniques include T-stenting, reverse T-stenting, Crush stenting, Culotte stenting, and simultaneous kissing stents. In such techniques two stents may be joined. Examples of methods of joining stents include ultrasonic welding, gluing, tying, bending, crimping, and interweaving [Estrada, et. al., 2014, Interventional Cardiology Review, 9, 1, 17-22].

In some embodiments, the method further comprises inflating the balloon to a sub-critical diameter, thereby expanding the balloon-expandable body portion and the self-expandable trumpet portion to a diameter less than the critical diameter thereby not breaking the breakable cover and not allowing the self-expandable trumpet portion to self-expand. Such a step may be advantageous for proper position of the bifunctional expandable stent by a medical professional. Such a step allows for visualization and testing of the proper positioning and orientation of the stent without committing to breaking the breakable cover and deploying the stent. A sub-optimally placed or oriented stent may be reposition or reoriented by deflation of the balloon, appropriate changes to position and/or orientation, and re-inflation of the balloon.

In some embodiments, the method further comprises retrieving the breakable cover. In such embodiments, the breakable cover may be retrieved by any suitable method or with any suitable device known to one of ordinary skill in the art, such as a laparoscopic tool or catheter.

Alternatively, the breakable cover may be attached to a catheter or guidewire that the bifunctional stent delivery assembly is attached to or disposed upon. In such embodiments, the breakable cover, once broken, is retrieved by an action of removing the catheter or guidewire.

The examples below are intended to further illustrate embodiments of the bifunctional stent delivery assembly and protocols for the method of stenting a patient in need of percutaneous coronary intervention at a bifurcation site and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Both trumpet and body portions of the stent have different sizes and combinations available to match different anatomies and for better conformability and apposition. The trumpet is sized according to the size of the main branch vessel and body is selected according to the diameter of the side-branch. Examples of the sizes and combinations of trumpet and body portion diameters are shown below. The below examples are not intended to constitute an exhaustive list of sizes or combinations.

| Trumpet (according to Main Branch Diameter) | Body (according to Side Branch Diameter) | | |
|---|---|---|---|
| 2.5 mm | 2.5 mm | | |
| 3.0 mm | 2.5 mm | 3.0 mm | |
| 3.5 mm | 2.5 mm | 3.0 mm | 3.5 mm |

Proper deployment of the bifunctional expandable stent may be accomplished by:
1) Positioning of stent into side branch with ostial marker at the ostium of the side branch.
2) Inflation of the balloon to deploy the balloon expandable part of the stent into the side branch, the same inflation splits the short breakable cover of the self expandable part of the stent, deploying the self expandable part of the stent, for optimal ostial coverage.
3) Retraction of the used balloon along with the attached short breakable cover.

The invention claimed is:

1. A bifunctional expandable stent delivery assembly, comprising:
   a bifunctional expandable stent comprising a balloon-expandable body portion configured to expand only by application of an expansion force thereto, a self-expandable trumpet portion configured to self-expand, and a drug-containing coating disposed on the balloon-expandable body portion and/or the self-expandable trumpet portion;
   a breakable cover which is configured to fit over only the self-expandable trumpet portion but not the balloon-expandable body portion and provide a compressive effect thereby preventing the self-expandable trumpet portion from self-expanding and maintaining the self-expandable trumpet portion its as a compressed trumpet; and
   a balloon located in an interior portion of the bifunctional expandable stent, and configured to expand by inflation so as to apply the expansion force to the balloon-expandable body portion to expand the balloon-expandable body portion and expand the self-expandable trumpet portion to a critical diameter at which the breakable cover is configured to break to allow the self-expandable trumpet portion to self-expand;
   wherein:
   the balloon-expandable body portion constructed of a first metal or metal alloy and having a body portion proximal end and a body portion distal end, the balloon-expandable body portion being compressible thereby forming a compressed cylinder having a body portion compressed diameter in a compressed state and expandable thereby forming an expanded tapered cylinder having a body portion proximal end expanded diameter and a body portion distal end expanded diameter in an expanded state, the body portion proximal end expanded diameter and the body portion distal end expanded diameter both being larger than the body portion compressed diameter;

the self-expandable trumpet portion is constructed of a second metal or metal alloy, comprises a plurality of rings, each ring includes a plurality of struts arranged about a circumference of the self-expandable trumpet portion, the rings connected by linkers, each linker being connected to two or more struts, the self-expandable trumpet portion has a trumpet portion fixed end connected to the body portion proximal end of the balloon-expandable body portion and a trumpet portion free end; and a plurality of anchoring portions disposed on the trumpet portion free end, the anchoring portions comprising struts which are flattened and enlarged compared to the struts of the self-expandable trumpet portion which are not anchoring portions;

the self-expandable trumpet portion is compressible thereby forming a compressed trumpet having a cylindrical shape with a compressed fixed end diameter and the compressed free end diameter, both of which are equal to the body portion compressed diameter of the balloon-expandable body portion in the compressed state; and the self-expandable trumpet portion is expandable, thereby forming an expanded trumpet having a cylindrically-symmetrical flange shape having an expanded fixed end diameter equal to the body portion proximal end expanded diameter of the proximal end of the balloon-expandable body portion and an expanded free end diameter greater than the body portion proximal end expanded diameter of the proximal end of the balloon-expandable body portion in the expanded state.

2. The bifunctional expandable stent delivery assembly of claim 1, wherein the self-expandable trumpet portion is configured to self-expand by a shape-memory effect.

3. The bifunctional expandable stent delivery assembly of claim 1, wherein the first metal or metal alloy is a cobalt-chromium alloy or a platinum-chromium alloy.

4. The bifunctional expandable stent delivery assembly of claim 1, wherein the second metal or metal alloy is a shape-memory alloy.

5. The bifunctional expandable stent delivery assembly of claim 4, wherein the shape-memory alloy is a Nitinol.

6. The bifunctional expandable stent delivery assembly of claim 1, wherein the drug-containing coating comprises a polymer and an antiproliferative drug.

7. The bifunctional expandable stent delivery assembly of claim 6, wherein the antiproliferative drug is at least one selected from the group consisting of Everolimus, Zotarolimus, Sirolimus, Biolimus and umirolimus.

8. The bifunctional expandable stent delivery assembly of claim 1, further comprising one or more radiopaque markers.

9. The bifunctional expandable stent delivery assembly of claim 1, wherein the breakable cover comprises a durable polymer.

10. The bifunctional expandable stent delivery assembly of claim 1, wherein the breakable cover comprises a biodegradable or bioresorbable polymer.

11. The bifunctional expandable stent delivery assembly of claim 1, further comprising a catheter, wherein the bifunctional expandable stent is attached to, integrated with, or disposed upon the catheter.

12. The bifunctional expandable stent delivery assembly of claim 11, wherein the breakable cover is attached to the catheter.

13. The bifunctional expandable stent delivery assembly of claim 1, wherein:

at least three anchoring portions are present and the anchoring portions are equally distributed about the trumpet portion free end.

14. The bifunctional expandable stent delivery assembly of claim 1, wherein the self-expandable trumpet portion comprises:

a continuous cone-shaped surface which is continuous about the circumference of the self-expandable trumpet portion; and a continuous endmost ring which is continuous about the circumference of the self-expandable trumpet portion.

15. A method of stenting a patient in need of percutaneous coronary intervention at a bifurcation site, comprising:

placing into a branch of a bifurcation site the bifunctional expandable stent delivery assembly of claim 1 such that the balloon-expandable body portion is oriented downstream of the bifurcation site and the self-expandable trumpet portion is located at the bifurcation site; and inflating the balloon to the critical diameter, thereby expanding the balloon-expandable body portion and the self-expandable trumpet portion to the critical diameter at which the breakable cover breaks to allow the self-expandable trumpet portion to self-expand.

16. The method of claim 15, wherein the bifurcation site comprises a side branch lesion.

17. The method of claim 15, wherein the bifurcation site has a bifurcation lesion having a Medina classification of (X, Y, 1), where X=0 or 1 and Y=0 or 1.

18. The method of claim 15, wherein the balloon-expandable body portion is oriented in a side branch of the bifurcation site and the self-expandable trumpet portion is located at a carina of the bifurcation site.

19. The method of claim 15, wherein the method further comprises inflating the balloon to a sub-critical diameter, thereby expanding the balloon-expandable body portion and the self-expandable trumpet portion to a diameter less than the critical diameter thereby not breaking the breakable cover and not allowing the self-expandable trumpet portion to self-expand.

20. The method of claim 15, further comprising retrieving the breakable cover.

* * * * *

UNITED STATES PATENT AND TRADEMARK OFFICE
CERTIFICATE OF CORRECTION

| | |
|---|---|
| PATENT NO. | : 11,672,683 B2 |
| APPLICATION NO. | : 17/062836 |
| DATED | : June 13, 2023 |
| INVENTOR(S) | : Muhammad Fayaz Khan |

It is certified that error appears in the above-identified patent and that said Letters Patent is hereby corrected as shown below:

On the Title Page

Item (73), the Assignee's information is incorrect. Item (73) should read:
--(73) Assignees: National Guard Health Affairs, Riyadh (SA); King Saud bin Abdulaziz University for Health Sciences, Riyadh (SA); King Abdullah International Medical Research Center, Riyadh (SA)--

Signed and Sealed this
Tenth Day of October, 2023

Katherine Kelly Vidal
*Director of the United States Patent and Trademark Office*